United States Patent
Wang et al.

(10) Patent No.: US 7,495,762 B2
(45) Date of Patent: Feb. 24, 2009

(54) HIGH-DENSITY CHANNELS DETECTING DEVICE

(75) Inventors: Hau-Wei Wang, Taipei County (TW);
Fu-Shiang Yang, Hsinchu County (TW);
Ding-Hsiang Pan, Kaohsiung County (TW)

(73) Assignee: Industrial Technology Research Institute, Hsinchu (TW)

( * ) Notice: Subject to any disclaimer, the term of this patent is extended or adjusted under 35 U.S.C. 154(b) by 262 days.

(21) Appl. No.: 11/469,904

(22) Filed: Sep. 5, 2006

(65) Prior Publication Data

US 2007/0165210 A1    Jul. 19, 2007

(30) Foreign Application Priority Data

Jan. 13, 2006    (TW) .............................. 95101406 A

(51) Int. Cl.
*G01J 3/28* (2006.01)
(52) U.S. Cl. .................. 356/328; 356/630; 356/632
(58) Field of Classification Search ................. 356/326, 356/328
See application file for complete search history.

(56) References Cited

U.S. PATENT DOCUMENTS

| 4,676,647 | A  | 6/1987 | Kikkawa et al. |
| 5,555,474 | A  | 9/1996 | Ledger |
| 2002/0030826 | A1 | 3/2002 | Chalmers et al. |
| 2005/0162649 | A1 | 7/2005 | Kryszczynski et al. |

FOREIGN PATENT DOCUMENTS

| JP | 01-147306 | 6/1989 |
| TW | 1245114 | 12/2005 |

*Primary Examiner*—F. L Evans
(74) *Attorney, Agent, or Firm*—Jianq Chyun IP Office

(57) ABSTRACT

A high-density channels detecting device for detecting a sample is provided. The high density detecting-device has a light source for emitting a light beam, a collimator, a beam splitter, and a high-density channels imaging device. The collimator arranged on the beam path is used for collimating the emitted light beam. The beam splitter reflects the light beam incident from the collimator to the sample, and the light beam reflected by the sample passes through the beam splitter. The imaging device receives the light beam passing through the beam splitter, and has a light collector and a multi-channel kernel module for receiving the light beam from the light collector. By using the light collector, the light beam incident to the kernel module is parallel to the optical axis of the kernel module.

27 Claims, 9 Drawing Sheets

HIGH-DENSITY CHANNELS DETECTING DEVICE

CROSS-REFERENCE TO RELATED APPLICATION

This application claims the priority benefit of Taiwan application serial no. 95101406, filed Jan. 13, 2006. All disclosure of the Taiwan application is incorporated herein by reference.

BACKGROUND OF THE INVENTION

1. Field of the Invention

The present invention relates to a sample detecting device. More particularly, the present invention relates to a high-density channels detecting device.

2. Description of Related Art

The thin film quality detecting technology, including measurements of optical constants, such as thin film thickness, optical refraction indexes, and extinction coefficients, plays an important role not only in semiconductor manufacturing processes, but also in liquid crystal display manufacturing processes.

Currently, the conventional thin film quality detecting device can be substantially classified into a single point thin film measuring device, a filtering image thin film measuring device and a multi-channel thin film measuring device, etc. FIG. 1 shows a single point thin film measuring device disclosed in U.S. Pat. No. 4,676,647. In the device, a light beam emitted from a light source 5 is irradiated to a sample 2 on a carrier 3, and the sample comprises a substrate or a thin film disposed on a substrate. The light beam is reflected by the sample 2, and then incident to a concave diffraction grating 8. A photodiode array detector 16 receives an optical signal, so as to obtain a reflection spectrum of the sample. Information of the single point film quality was acquired through a software algorithm. Though the architecture for the method is simple, a probe or the sample should be moved to collect the thin film information everywhere on the sample in order to obtain the information of the thin film quality of the whole test object, which takes a quite long time to detect. As a result, the method cannot be used in online detection.

FIG. 2 shows a thin film measuring device of filter image type, disclosed in U.S. Pat. No. 5,555,474. As shown in FIG. 2, the device mainly comprises a light source LS1, lenses L1 and L2, a filter wheel 24, a lens system 27, a beam splitter 26, etc. The filter wheel 24 is rotated during a measuring process. Since each filter 20 is a bandpass filter with different wavelength coverage from each other, after all filters 20 are rotated, a two-dimensional CCD 25 can shoot image information of a sample 23 at different wavelengths under different filters. The two-dimensional film quality measurement is obtained through a software algorithm. However, since rotating the filters takes time and the bandpass coverage of the filters is too broad, and the number of the filters is limited, the spectral resolution is low and the accuracy of the film quality measurement is limited. The two disadvantages both restrict the device to be used in online detection.

FIG. 3 shows a multi-channel thin film measuring device disclosed in U.S. Patent Application No. 20020030826. As shown in FIG. 3, the device utilizes a grating imaging spectrometer architecture. The parallel light reflected from the sample passes through a lens 34, a slit 35 and a lens 36, and then is incident to a grating 37. Subsequently, a detector 38 generates multiple spectral data. In FIG. 3, the perpendicular direction of the detector 38 represents the spatial direction, and the horizontal direction represents the spectral direction. With this device, the multi-channel spectral information (i.e., multi-point spatial information) can be obtained simultaneously, and the multi-point thin film quality measurement is also achieved. In general, the principle for operating a grating is that the light beam should be incident in parallel to the grating. But in FIG. 3, since the lens is placed in front of the grating 37, the light beam cannot be incident to the grating in parallel, thereby extra aberration will be generated and the spectral resolution is thus degraded. The measurable spectral range can be equally divided into only 32 parts and the spectral resolution is limited, thereby negatively affecting the accuracy of the thin film quality measurement. Therefore, the device cannot be used in online detection, either.

In recent years, since the area of a thin film sample has become larger and the processing speed is fast, rapid and accurate detection has become more and more important. However, the single point thin film measuring method is mostly used among the existing thin film quality detecting technologies. Though the method is accurate, the probe or the test object should be moved to obtain two-dimensional film images, which spends a lot of time and cannot be used in online detection. Though the multi-channel film quality detecting method is developed to detect more rapidly later, the measurement accuracy is low due to the aberration. Therefore, the method cannot be used in online detection, either.

In view of the aforementioned methods, no online thin film detecting device has achieved a multi-channel and rapid measurement as well as an accurate measurement of film quality. Therefore, up to now, no device has achieved the purposes of accurate measurement of thin film and rapid measurement. As a result, a new measurement method is highly desirable.

SUMMARY OF THE INVENTION

Accordingly, one object of the present invention is to provide a high-density channels detecting device for solving the problems in the conventional art that the multi-channel rapid measurement and accurate measurement of film quality cannot be achieved simultaneously. Meanwhile, an online detection device is established to achieve the functions of high spectral resolution and multi-channel measurement.

In order to achieve the above object, the present invention provides a high-density channels detecting device for detecting a sample. The high-density channels detecting device comprises at least a light source, a collimator, a beam splitter, and a high-density channels spectral imaging device. The light source is used for emitting a light beam. The collimator is arranged in front of the light source and on a beam path of the light beam for collimating the light beam as a parallel light beam. The beam splitter reflects the light beam incident from the collimator to the sample and the light beam reflected by the sample passes through the beam splitter. The high-density channels spectral imaging device is arranged to receive the light beam transmitted through the beam splitter and detects the sample. The high-density channels spectral imaging device comprises a light collector and a multi-channel kernel module for receiving the light beam from the light collector. By using the light collector, the light beam incident to the multi-channel kernel module is parallel to an optical axis of the multi-channel kernel module.

According to one embodiment of the present invention, the present invention further provides a high-density channels detecting device for detecting a transparent sample, for enhancing the accuracy of film quality measurement. The high-density channels detecting device comprises at least a light source, a collimator, a reflecting mirror, and a high-density channels spectral imaging device. The light source is used for emitting a light beam. The collimator is arranged in front of the light source and on the beam path of the light beam for collimating the light beam as a parallel light beam. The reflecting mirror reflects the light beam incident from the collimator to the sample. The high-density channels spectral imaging device is arranged to receive the light beam passed through the beam splitter and detects the sample. The high-density channels spectral imaging device comprises a light collector and a multi-channel kernel module for receiving the light beam from the light collector. By using the light collector, the light beam incident to the multi-channel kernel module is parallel to an optical axis of the multi-channel kernel module.

According to one embodiment of the present invention, the present invention further provides a high-density channels detecting device for detecting a sample. The high-density channels detecting device comprises a light source, a first optical fiber bundle, multiple optical fiber probes, and a high-density channels spectral imaging device. The light source is used for emitting a light beam. The first optical fiber bundle has multiple branched optical fiber bundles for splitting the light beam into multiple light beams. Each optical fiber probe comprises an input end, an input/output end, and an output end. Each input end is coupled to each branched optical fiber bundle of the first optical fiber bundle for receiving each split light beam, and the input/output end is arranged at position over the corresponding test points of the corresponding sample, so as to irradiate each split light beam onto each measuring point and receive each light beam reflected from each measuring point. The high-density channels spectral imaging device comprises a second optical fiber bundle and a multi-channel kernel module for receiving the light beams from the second optical fiber bundle. The second optical fiber bundle comprises multiple branched optical fiber bundles respectively coupled to the output ends of the optical fiber probes, for receiving each light beam reflected from each measuring point. Through the second optical fiber bundle, the light beams incident to the multi-channel kernel module are parallel to an optical axis of the multi-channel kernel module.

According to a further embodiment of the present invention, the present invention further provides a high-density channels detecting device for detecting a sample. The high-density channels detecting device comprises a light source, a first optical fiber bundle, multiple first optical fiber probes, multiple second optical fiber probes, and a high-density channels spectral imaging device. The light source is used for emitting a light beam. The first optical fiber bundle has multiple branched optical fiber bundles for splitting the light beam into multiple light beams. Each first optical fiber probe comprises an input end and an output end. The input ends are respectively coupled to the branched optical fiber bundles of the first optical fiber bundle for receiving light beams, and the output end is arranged on multiple measuring points of the corresponding sample for irradiating the light beams onto the measuring points. Each second optical fiber probe comprises an input end and an output end, in which the input ends are respectively arranged at position over the corresponding measuring points of the sample for receiving the light beam passed through each test point. The high-density channels imaging device comprises a second optical fiber bundle and a multi-channel kernel module for receiving the light beams from the second optical fiber bundle. The second optical fiber bundle comprises multiple branched optical fiber bundles respectively coupled to the output ends of the second optical fiber probes to receive each light beam passed through each measuring point. Through the second optical fiber bundle, the light beams incident to the multi-channel kernel module are parallel to the optical axis of the multi-channel kernel module.

Through the high-density channels detecting device of the present invention, the characteristics of multiple channels and high spectral resolution are achieved simultaneously, and spatial channels can be achieved. The spectral range to be measured can be equally divided into more than one hundred parts, thereby a high spectral resolution can be achieved. The measured information of the thin film reflection or the transmission spectrum of each channel can be used to get a one-dimensional continuous or discrete multi-channel thin film quality information in a linear field of view simultaneously and accurately, through a software algorithm. Additionally, the one-dimensional film quality information in the linear field of view can be further combined into a two-dimensional film quality information by moving the probes or the sample. Furthermore, transparent or opaque samples can be detected according to the arrangement of the high-density channels imaging device, thereby the applicability can be greatly enhanced.

In order to make the aforementioned and other objects, features and advantages of the present invention comprehensible, preferred embodiments accompanied with drawings are described in detail below.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

Figure 4:
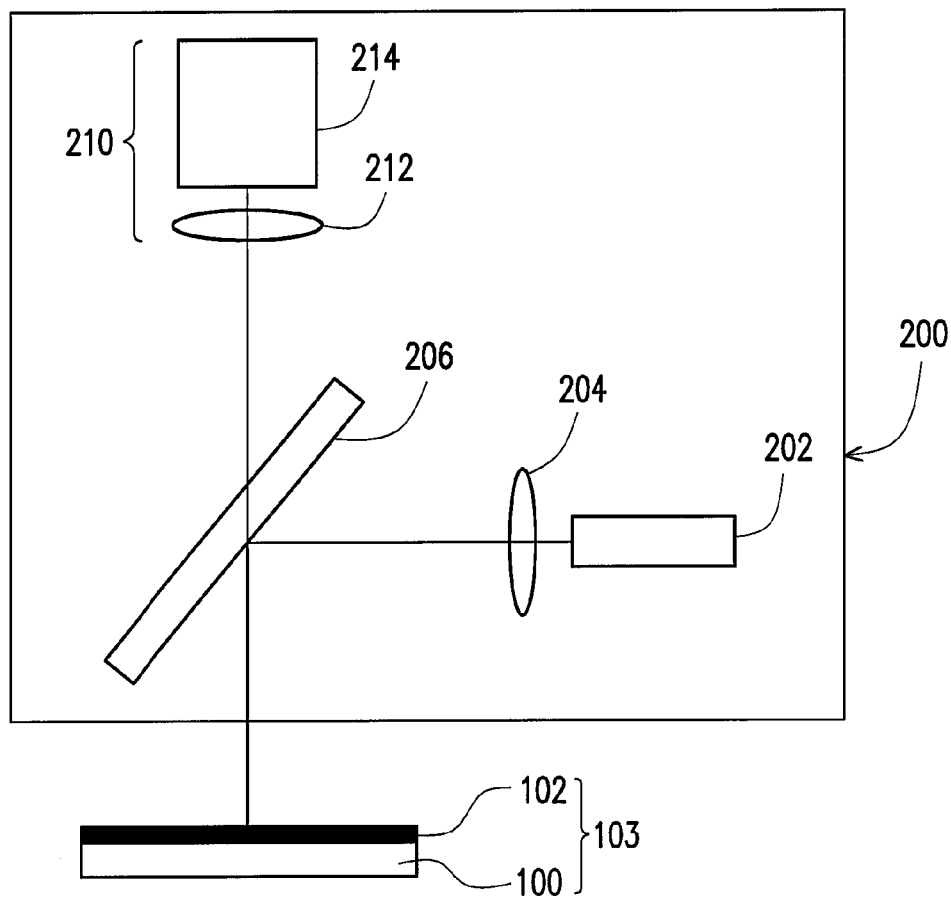
FIG. 4 is a schematic view showing an architecture of a high-density channels detecting device according to one embodiment of the present invention.

FIG. 4 is a schematic structure view showing a high-density channels detecting device according to one embodiment of the present invention. The structure of the high-density channels detecting device 200 comprises at least a light source 202, a collimator 204, a beam splitter 206, and a high-density channels spectral imaging device 210. The high-density channels spectral imaging device 210 further comprises a light collector 212 and a multi-channel kernel module 214. Preferably, the light source is a broadband white light source with each wavelength component smoothly distributed in the spectrum, such as a halogen lamp.

The light beam emitted from the light source 202 first passes through the collimator 204, and is approximately collimated a linear and parallel light beam. The collimated light beam is then incident to the beam splitter 206. The beam splitter 206 reflects the light beam onto a thin film (sample) 102 on a substrate 100, i.e., an object to be tested. The sample 102 to be tested may be a single-layer thin film or a multi-layer thin film on a glass substrate or a silicon substrate. The interference light reflected from the sample is finally collected by the high-density channels spectral imaging device 210 to analyze the characteristic of the film quality of the thin film 102 to be tested.

Figure 5:
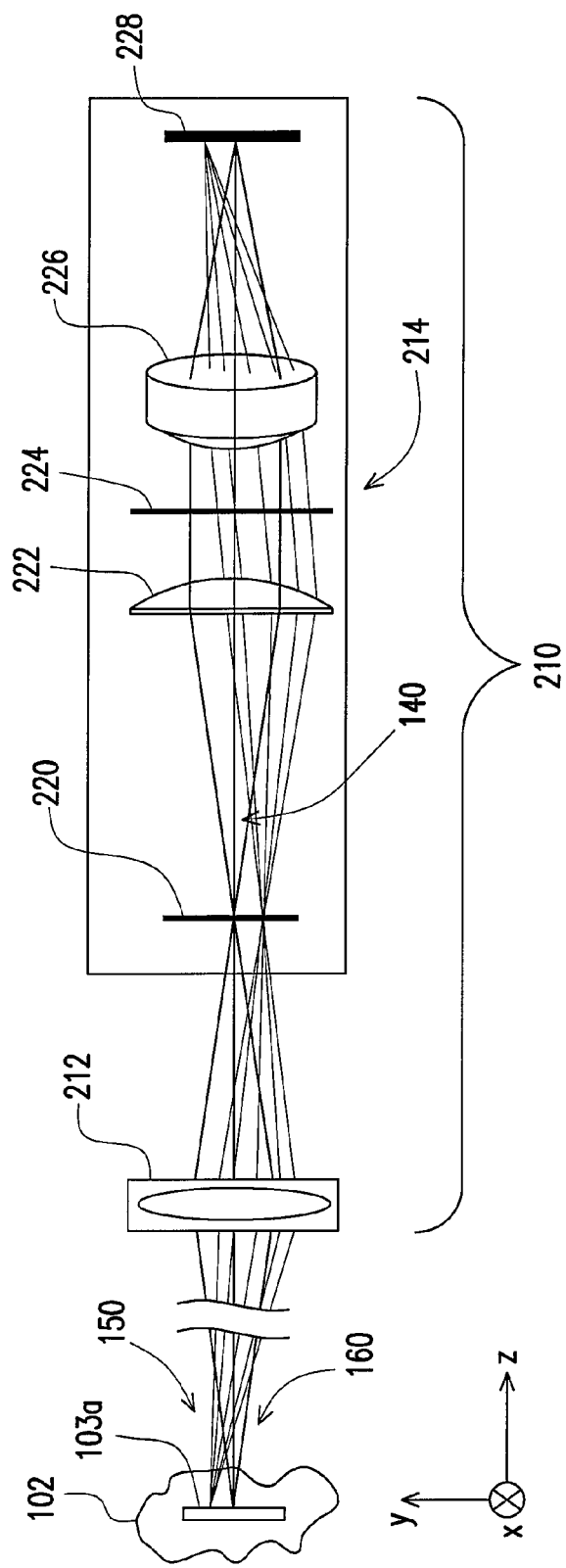
FIG. 5 is a schematic view showing an architecture of the high-density channels spectral imaging device according to one embodiment of the present invention for illustrating the operation mode.

FIG. 5 is a schematic structure view showing the high-density channels spectral imaging device 210 for illustrating the operation according to one embodiment of the present invention. The high-density channels spectral imaging device 210 comprises a light collector 212 and a multi-channel kernel module 214. In the embodiment, the light corrector 212 comprises an image-side telecentric lens 212 or a general focusing lens. The multi-channel kernel module 214 comprises an optical slit 220, a collimator lens 222, a diffraction grating 224, a focusing lens 226, and a two-dimensional array sensor 228. The collimator lens 222 can be an aspherical collimator lens or a spherical collimator lens, the diffraction grating 224 can be a transmission diffraction grating or a reflection diffraction grating, and the focusing lens 226 can be a general focusing lens or an achromatic focusing lens. As shown in FIG. 5, after the principle rays emitted from each point in a linear field of view 103a on the object side (sample) 103 are converted to be parallel to an optical axis 140 through the image-side telecentric lens 212, the principle rays are incident to the optical slit 220 in the multi-channel kernel module 214. After passing through the optical slit 220, the light beam is further incident to the collimator lens 222 and approximately becomes collimated light beam. Then, the collimated light beam is further incident to the diffraction grating 224 and reaches the two-dimensional array sensor 228 through the focusing lens 226.

Figure 1:
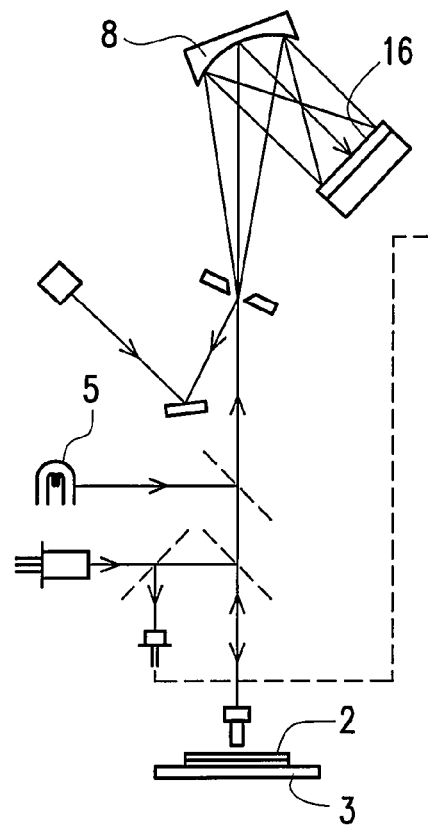
FIG. 1 shows a conventional single point thin film measuring device.
Figure 2:
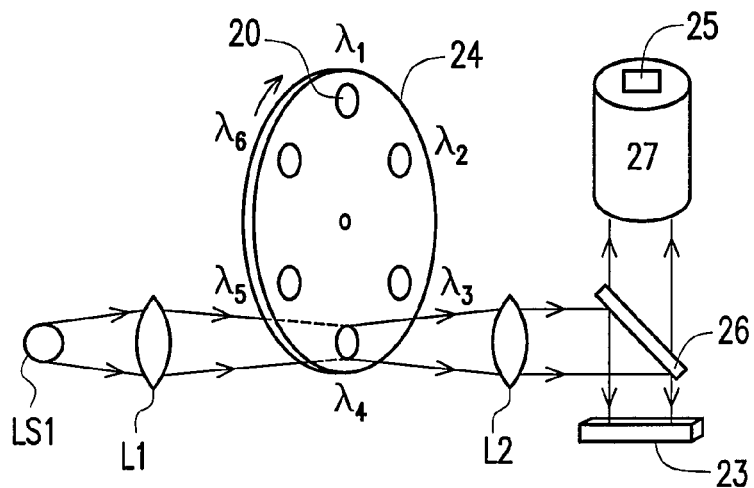
FIG. 2 shows a conventional filtering image thin film measuring device.
Figure 3:
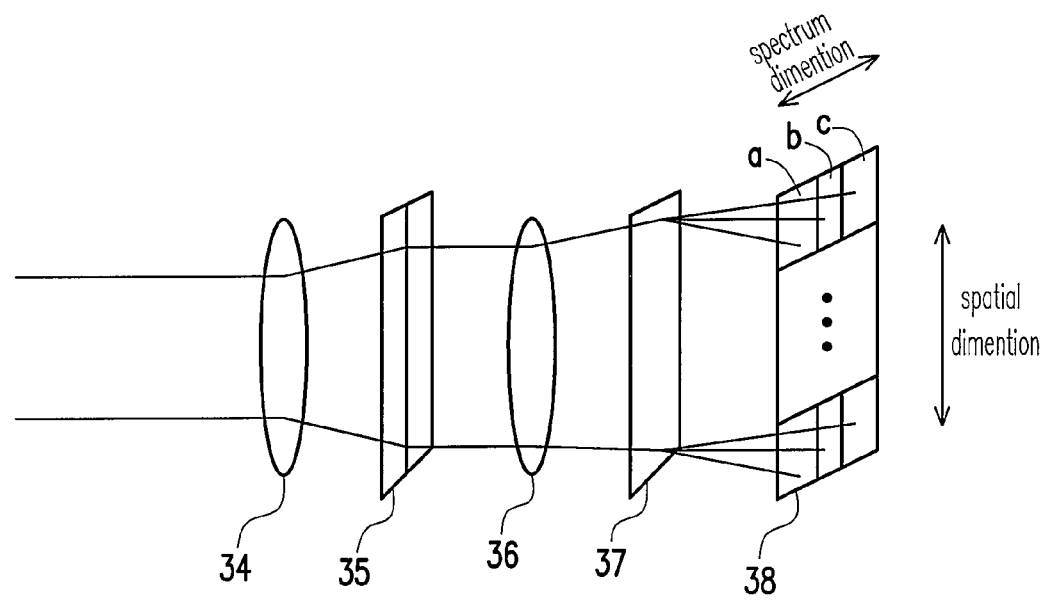
FIG. 3 shows a conventional multi-channel thin film measuring device.

Because the principle rays emitted from each point in the field of view 103a on the object side (sample) 103 become parallel to the optical axis 140 through the image-side telecentric lens 212, and the incident light beam is approximately collimated through the collimator lens 222, the light beam incident to the grating 224 is a collimated light beam, which satisfies the operational conditions of the grating. Therefore, the problem in the conventional structure as shown in FIG. 3 is solved; that is, the light beam incident to the grating is not a parallel light beam can be solved. Additionally, the present invention further utilizes a combination using achromatic lens 226 and tilting the sensor 228 to adjust an inclined position of the chromatic aberration surface, so that the chromatic aberration at each wavelength band can also be eliminated. Through the aforementioned structure, the light emitted from the on-axis 160 or the off-axis 150 in the linear field of view 103a at the object side only has tiny aberration, so that the spectral resolution is considerably enhanced to achieve the purposes of high density and multiple channels.

Figure 6:
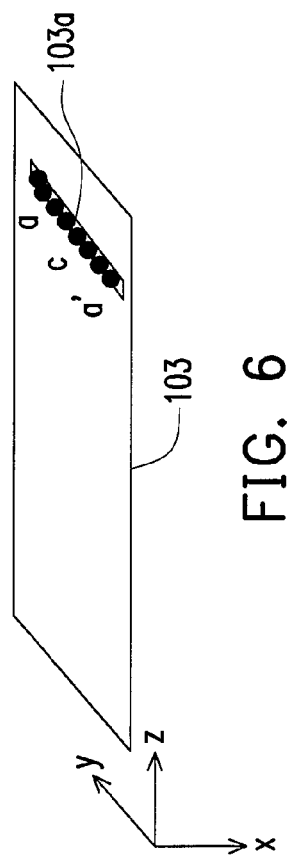
FIG. 6 is a schematic view showing a field of the high-density channels spectral imaging device on the sample.
Figure 7:
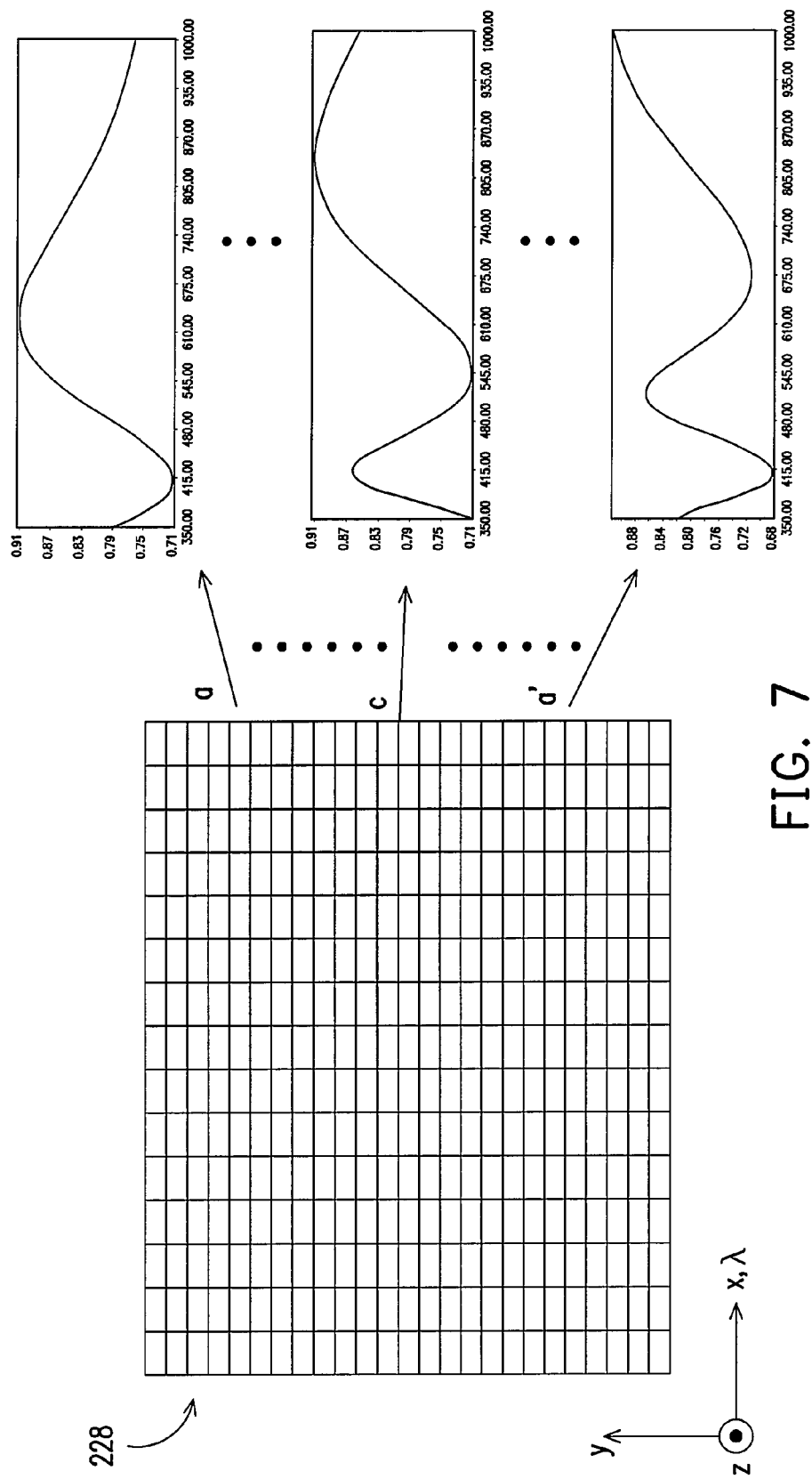
FIG. 7 is a plan view of the two-dimensional array sensor and schematic views of the measuring results of the measuring points.

FIG. 6 is a schematic a field of view of the high-density channels spectral imaging device on the sample. The field of view of the high-density channels spectral imaging device 210 on the sample 103 end is linear. That is, in the present invention, a linear area (multiple measuring points arranged in a row) on the sample 103 is used as an object to be measured when the sample is detected. FIG. 7 is a plan view of the two-dimensional array sensor 228 and schematic diagrams of the measuring results at each measuring point.

Next, the measurement operation of the multi-channel spectrum of the present invention is illustrated in accordance with FIGS. 6 and 7. FIG. 7 shows the plan view of the two-dimensional array sensor 228 in the left side, in which y-axis represents each measuring point on the linear field of view, and x-axis represents the spectral analysis at each wavelength. Points a, c, and a' in the linear field of view shown in FIG. 6 are used as examples. For a specific wavelength λ (i.e., x-axis of the two-dimensional array 228), the detecting points on the two-dimensional array 228 are used to detect the three corresponding positions a, c, and a' shown in FIG. 6. The detection results of the three measuring points a, c, and a' corresponding to the wavelength λ are shown in three spectral curves at the right side of FIG. 7.

That is, as shown in FIG. 7, for the image obtained on the two-dimensional array sensor 228, one axis corresponds to spatial channel information of the linear field of view 103a on 102, and the other axis corresponds to interference spectral information of the thin film sample 102. In the high-density channels spectral imaging device 210 as shown in FIG. 5, since the image-side telecentric lens 212 is used and the collimator lens 222, the focusing lens 226, and the two-dimensional array sensor 228 are tilted, light collected by not only the on-axis point c, but also the off-axis points a and a' in the object space 103a can be split on the sensor 228 shown in FIG. 7 (only three channels are shown as an example).

Therefore, the characteristics of multiple channels and high spectral resolution are achieved simultaneously, in which scores of spatial channels can be achieved and the channels are arranged continuously and tightly. The spectral range to be measured can be equally divided into more than one hundred parts, so as to achieve a high spectral resolution. The interference spectral information of the measured thin film of each channel can be further computed through a software algorithm, such as a library model based algorithm. The library model based algorithm is generated based on the electromagnetic wave theory. Then, some parameters, such as the distribution range of optical constants and intervals of optical constants, are given by a user, and the user further inputs given parameters, such as refractive index of materials, extinction coefficient, film layer thickness, incident angle, polarization of light, etc., to generate a database with thousands of data. A most approximate matching process is conducted between the database and the practically measured spectrum to get a most approximate theoretic spectrum, whose parameters contained therein, such as refractive index, extinction coefficient, and film layer thickness, are the values measured by the user. In this way, the one-dimensional continuous multi-channel thin film quality information in the linear field can be obtained simultaneously and accurately.

Additionally, the one-dimensional film quality information in the linear field 103a can be further combined into a two-dimensional film quality information by moving the probe or the sample 103.

Figure 11:
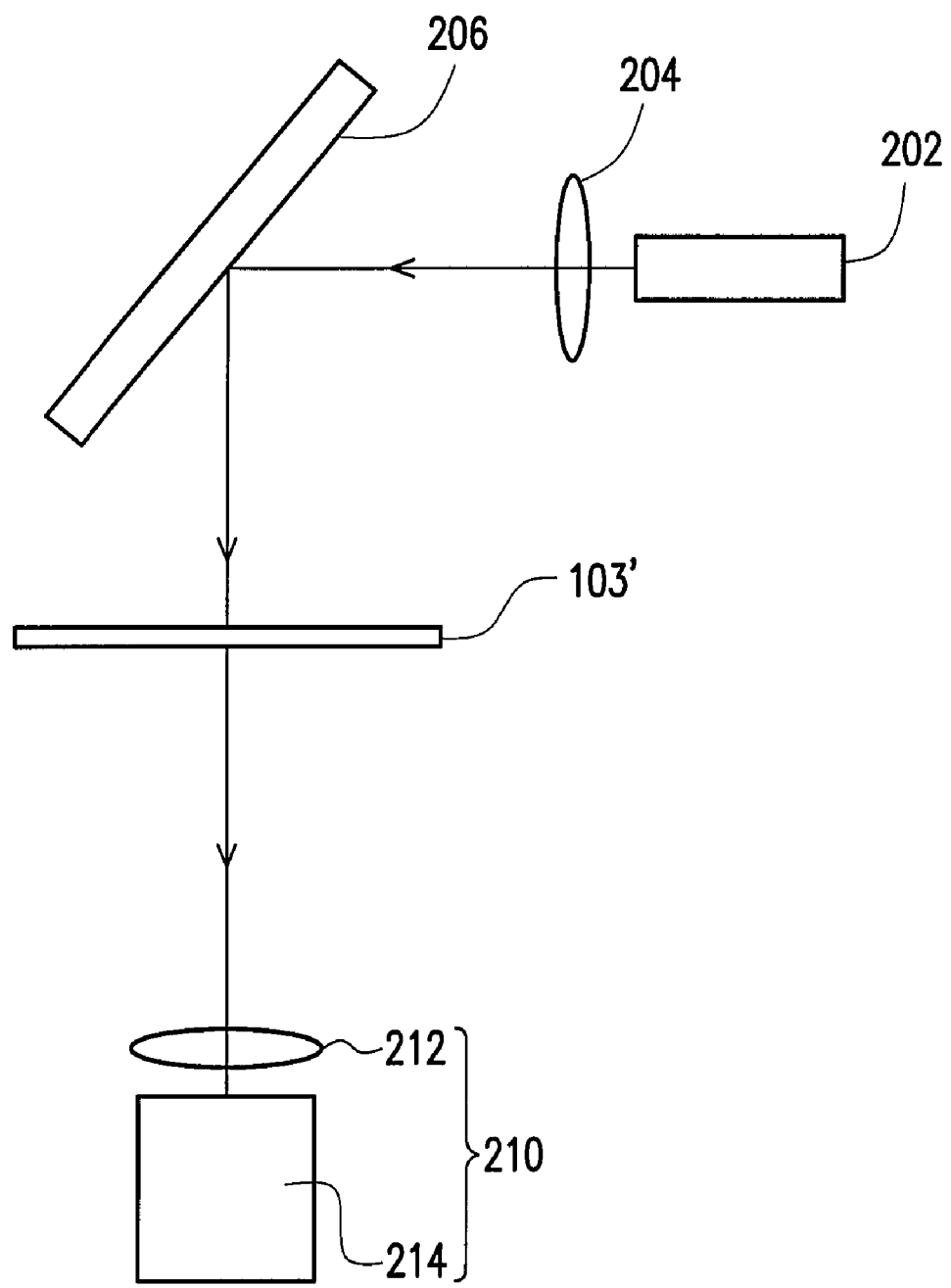
FIG. 11 is a schematic view of an alternative example of the high-density channels detecting device in FIG. 4.

Furthermore, as described above, an opaque thin film or substrate is taken as an example. The architecture in FIG. 4 can be slightly modified to detect a transparent sample. FIG. 11 is an alternative example of FIG. 4. As shown in FIG. 11, when measuring a transparent sample, the high-density channels spectral imaging device 210 is arranged under the sample 103' for receiving the light beam passing through the sample 103'. The method for measuring the transparent sample is substantially the same as that of the opaque sample and will not be further described in detail. Additionally, since the sample is light transmissible, the beam splitter may be replaced by a common reflection mirror.

Figure 8:
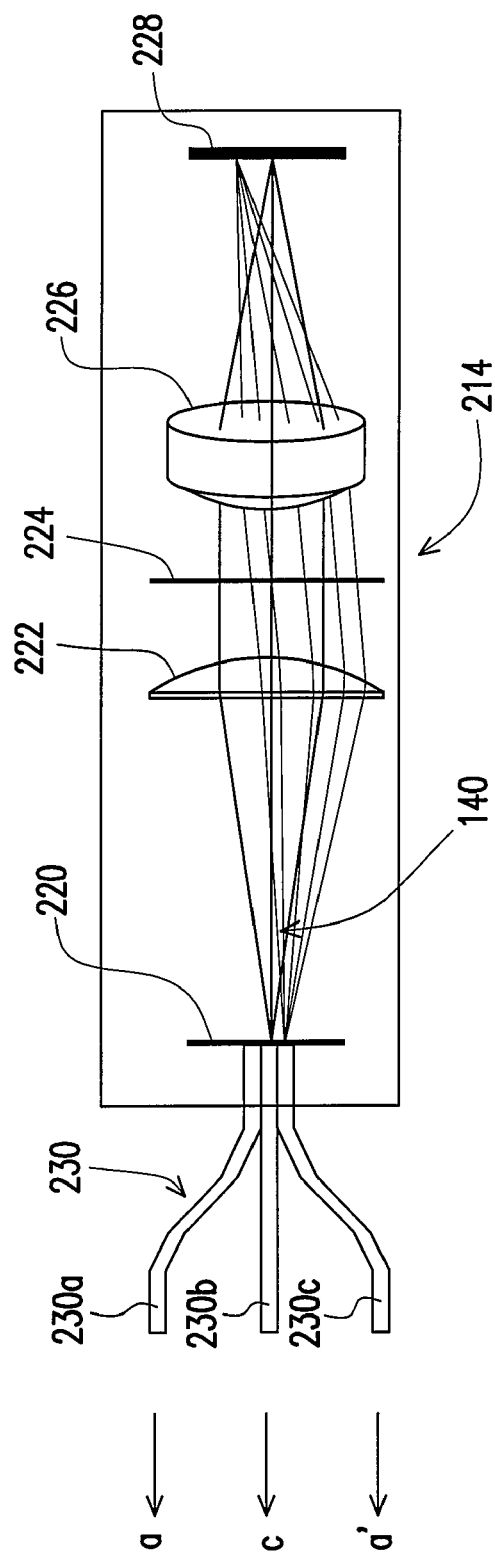
FIG. 8 is a schematic view showing an architecture of the kernel module in the high-density channels detecting device according to a further embodiment of the present invention.

FIG. 8 is a schematic view showing an architecture of the kernel module in the high-density channels detecting device according to another embodiment of the present invention. The high-density channels detecting device shown in FIG. 4 is a continuously detecting device and the measuring points are continuously distributed in the linear field. On the contrary, FIG. 8 shows a discreet structure and the measuring points are distributed randomly and not continuously.

The kernel modules in FIGS. 8 and 5 are different in the light collector. In FIG. 8, a multi-core optical fiber bundle is used as the light collector in FIG. 4. For the multi-core optical fiber bundle 230, three optical fiber bundles 230a, 230b, and 230c are shown in FIG. 8 as an example, but the practical number may be suitably increased or decreased according to the practical measurement. The optical fiber bundles 230a, 230b, and 230c are mainly arranged close to the measuring points for receiving the light beam reflected by or passing through the measuring points. The light beams received by the optical fiber bundles 230a, 230b, and 230c further pass through the optical slit 220, the collimator lens 222, the diffraction grating 224, and the focusing lens 226, and finally reaches the two-dimensional array sensor 228. The principle rays of each of channels received from the optical fiber bundles 230a, 230b, and 230c are incident to the multi-channel kernel module 214 in parallel to the optical axis 140, so that the aberration of the on-axis light and the off-axis light on the sensor is tiny. In this way, the characteristics of multiple channels and high spectral resolution can exist simultaneously.

Figure 9:
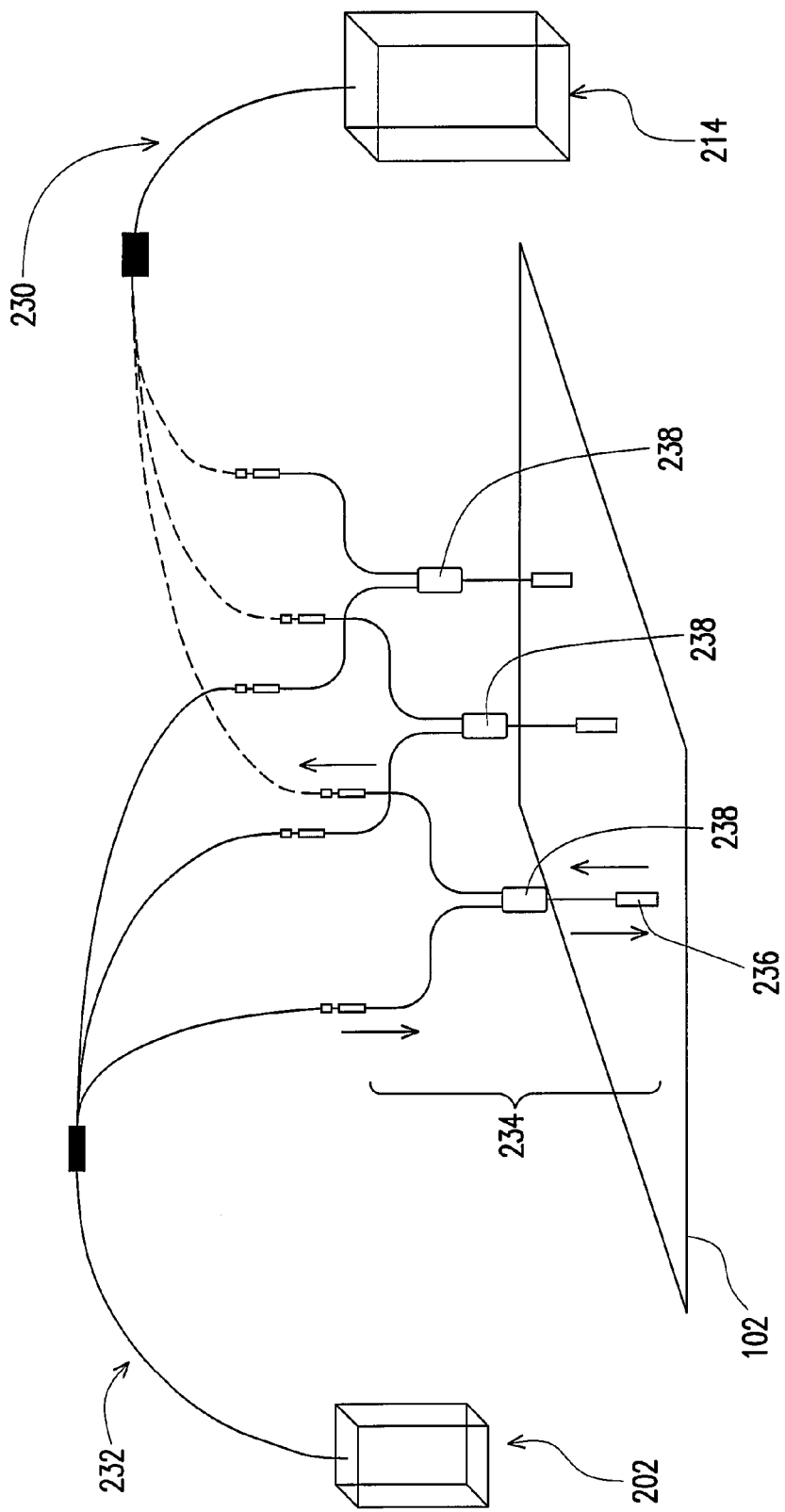
FIG. 9 is a schematic view showing an architecture of the high-density channels detecting device according to a further embodiment of the present invention.
Figure 10A:
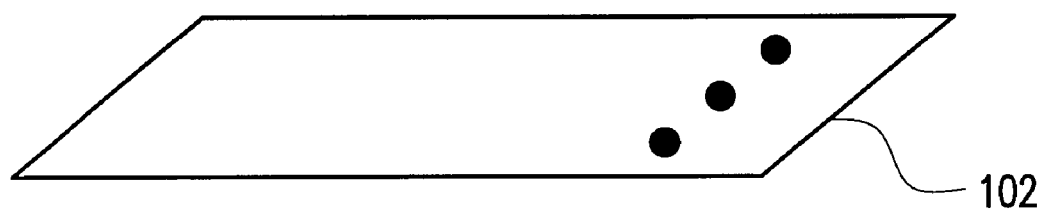
FIG. 10A is a schematic view of the distribution of the one-dimensional discreet multi-channel optical fiber probe of the high-density channels detecting device in FIG. 9.

FIG. 9 is a schematic view showing an architecture of the high-density channels detecting device according to another embodiment of the present invention. As shown in FIG. 9, the light source 202 is a broadband white light source, such as a halogen lamp. The light beam emitted by the broadband white light source is split into three channels through a trifurcated fiber bundle 232, wherein three channels are only an example and does not intend to limit the scope of the present invention. Then the light beams are guided to a collimator 236 through a bifurcated fiber bundle 238, respectively, and incident to an object 103 to be measured in parallel. The object 103 to be measured can be a single-layer thin film or a multi-layer thin film on a glass substrate or a silicon substrate. The bifurcated fiber bundle 238 and the collimator 236 form an optical fiber probe 234. The optical fiber probe 234 comprises an input end on the bifurcated fiber bundle 238, an input/output end on the collimator 236 and an output end on the bifurcated fiber bundle 238. Each input end is coupled to each branched optical fiber bundle of the optical fiber bundle 232 to receive each light beam, and the input/output end is correspondingly arranged over multiple measuring points on the sample, so as to irradiate each light beam onto each measuring point and receive the spectrum reflected from each measuring point. As shown in FIG. 10A, the optical fiber probes 234 may be arranged into a one-dimensional discrete multi-channel mode and be responsible for emitting and receiving light beams.

After being emitted from the light source 202, the light beam is split into three light beams by the trifurcated fiber bundle 232. Each light beam reaches the collimator 236 through the bifurcated fiber bundle 238 of the optical fiber probe 234, and then irradiates onto the measuring points of the sample 102 through the collimator 236. Subsequently, the light beam reflected by the thin film is incident to the measuring point, and also received by the optical fiber probe 234. The reflected light beam is incident to the multi-core optical fiber bundle 230 through the collimator 236 and the bifurcated fiber bundle 238, for coupling the multi-channel signal into the kernel module 214. Since the principle rays of each channel are incident into the multi-channel kernel module 214 in parallel to the optical axis 140, the aberration of the on-axis light and the off-axis light on the sensor is tiny due to the multi-channel kernel module 214, so that the characteristics of multiple channels and high spectral resolution are achieved simultaneously. The thin film interference spectral information of each channel may be computed through a software algorithm, such as a library model based algorithm. In this way, the thin film quality information can be obtained simultaneously and accurately by using the one-dimensional discrete multi-channel form.

Figure 10B:
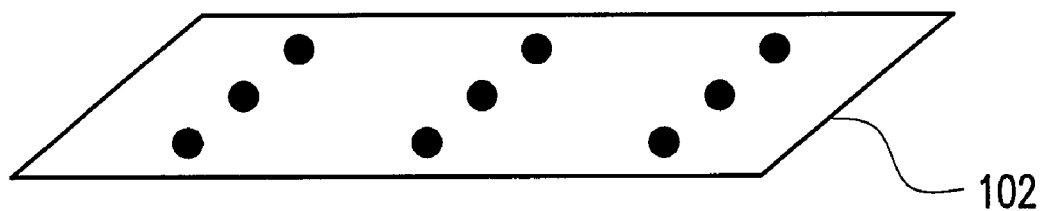
FIG. 10B is a schematic view of the distribution of the two-dimensional discreet multi-channel optical fiber probe of the high-density channels detecting device in FIG. 9.

Furthermore, if the optical fiber probe 234 or the sample 102 is further moved, the one-dimensional film quality information in FIG. 10A can be combined into a two-dimensional discrete film quality information. Additionally, as shown in FIG. 10B, an array of the optical fiber probes 234 can be distributed on the measuring thin film sample 102 (nine channels are shown as an example, but not to limit the scope of the present invention). In this way, without scanning, i.e., moving the optical fiber probe 234 and the test object 102, the two-dimensional discrete multi-channel thin film information of the sample 102 can be measured at one time.

Figure 12:
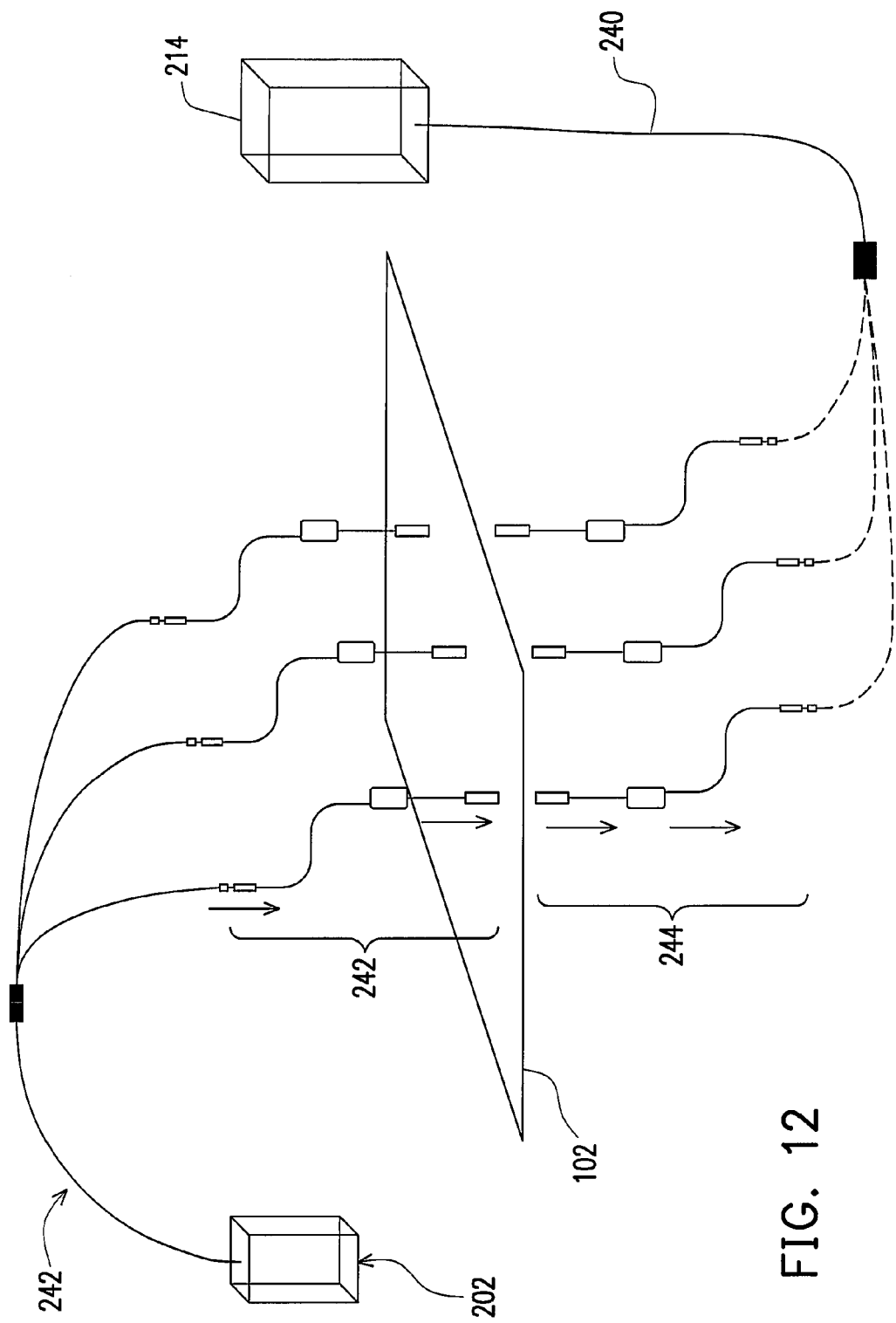
FIG. 12 is a schematic view of an alternative example of the high-density channels detecting device in FIG. 9.

Additionally, for an opaque sample, the reflection structure shown in FIG. 9 can be replaced by a transmission structure for conducting thin film transmission online detection. FIG. 12 is a schematic view of the transmission structure. Due to the transmission structure, the light beam incident to the sample 102 does not reach the multi-channel kernel module 214 along the path shown in FIG. 9. The optical fiber probe 242 in FIG. 9 comprises the optical fiber bundle 238 and the collimator 236. The optical fiber bundle 238 is unidirectional. Each optical fiber bundle of the multi-core optical fiber bundle 240 of the multi-channel kernel module 214 also comprises optical fiber probes 244, which are arranged under the sample 102 and opposite to the optical fiber probes 242, for receiving the light beams passing through the sample 102. The transparent samples can be measured through the changed transmission structure.

Additionally, supposing that the sample itself emits light, the light emitted from the sample can be directly received by the multi-channel kernel module without using an additional light source, thereby the aforementioned light source can be omitted.

The high-density channels method described in the aforementioned architectures is not limited to applications of the thin film detection. Any testing technology employing the spectrograph can utilize the method provided by the present invention. Therefore, the original single channel measurement can be expanded to the multi-channel measurement. The method can be directly used to measure the chromaticity and luminance of a flat panel display (FPD), measure the chromaticity and luminous intensity of the die of the light emitting diode (LED) of a semiconductor wafer, and detect the photoluminescence (PL) of a semiconductor wafer, such as a Si-based epi-layer, and a group III-V based epi-layer.

Additionally, supposing that the detection wavelength of the two-dimensional array sensor is designed to use a near infrared (NIR) wavelength, the two-dimensional array sensor can be used to the spectrographic detection of the pharmaceutics or textile. If the present invention further integrates with an optical coherence tomography (OCT) technology, the two-dimensional array sensor can be used to measure the three-dimensional configuration of inner skin. If further integrating with the polarization technology, the two-dimensional array sensor can be used to detect the characteristics of the birefringence of an FPD polarizer and measure the parameters of the spectroscopy ellipsometry of a thin film sample. Any multi-channel spectrographic detecting technologies are protected by the claims of the patent as long as the technologies employ multi-core optical fiber bundles or image-side telecentric lenses as light collectors.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A high-density channels detecting device for detecting a sample, comprising:
   a light source for emitting a light beam;
   a collimator lens arranged in front of the light source and on a beam path of the light beam for collimating the light beam as a parallel light beam and irradiating the collimated light beam onto the sample; and
   a high-density channels spectral imaging device, arranged to receive the light beam reflected from the sample so as to detect the sample, wherein the high-density channels spectral imaging device comprises a light collector and a multi-channel kernel module for receiving the light beam from the light collector, and by using the light collector, the light beam incident to the multi-channel kernel module is parallel to an optical axis of the multi-channel kernel module.

2. The high-density channels detecting device as claimed in claim 1, wherein a field of the high-density channels spectral imaging device on the sample is a one-dimensional linear field.

3. The high-density channels detecting device as claimed in claim 1, wherein the light source is a broadband white light source.

4. The high-density channels detecting device as claimed in claim 1, further comprising a beam splitter for reflecting the light beam emitted from the collimator to the sample such that the light beam reflected form the sample passes through the beam splitter.

5. The high-density channels detecting device as claimed in claim 1, wherein the multi-channel kernel module further comprises an optical slit, a collimator lens, a diffraction grating, a focusing lens and a two-dimensional array sensor arranged on the beam path of the light beam sequentially.

6. The high-density channels detecting device as claimed in claim 5, wherein the collimator lens is an aspherical collimator or a spherical collimator, the diffraction grating is a transmission diffraction grating or a reflection diffraction grating, and the focusing lens is a common focusing lens or an achromatic focusing lens.

7. The high-density channels detecting device as claimed in claim 6, wherein the achromatic focusing lens has a deviation angle about the optical axis of the multi-channel kernel module in an oblique manner.

8. The high-density channels detecting device as claimed in claim 6, wherein the two-dimensional array sensor tilts about the optical axis of the achromatic focusing lens.

9. The high-density channels detecting device as claimed in claim 1, the light collector is an image-side telecentric lens.

10. A high-density channels detecting device for detecting a sample, comprising:
    a light source for emitting a light beam;
    a collimator lens arranged in front of the light source and on the beam path of the light beam for collimating the light beam as a parallel light beam and irradiating the collimated light beam onto the sample; and
    a high-density channels spectral imaging device arranged to receive the light beam passing through the sample and for detecting the sample, wherein the high-density channels imaging device comprises a light collector and a multi-channel kernel module for receiving the light beam emitted from the collector, and by using the light collector, the light beam incident to the multi-channel kernel module is parallel to an optical axis of the multi-channel kernel module.

11. The high-density channels detecting device as claimed in claim 10, wherein a field of the high-density channels spectral imaging device on the sample is a one-dimensional linear field.

12. The high-density channels detecting device as claimed in claim 10, wherein the light source is a broadband white light source.

13. The high-density channels detecting device as claimed in claim 10, further comprising a reflecting mirror for reflecting the light beam emitted from the collimator to the sample.

14. The high-density channels detecting device as claimed in claim 10, wherein the multi-channel kernel module further comprises an optical slit, a collimator lens, a diffraction grating, a focusing lens, and a two-dimensional array sensor arranged on the beam path of the light beam sequentially.

15. The high-density channels detecting device as claimed in claim 14, wherein the collimator lens is an aspherical collimator or a spherical collimator, the diffraction grating is a transmission diffraction grating or a reflection diffraction grating, and the focusing lens is a common focusing lens or an achromatic focusing lens.

16. The high-density channels detecting device as claimed in claim 15, wherein the achromatic focusing lens has a deviation angle about the optical axis of the multi-channel kernel module in an oblique manner the two-dimensional array sensor tilts about the optical axis of the achromatic focusing lens.

17. The high-density channels detecting device as claimed in claim 10, wherein the light collector is an image-side telecentric lens.

18. A high-density channels detecting device for detecting a sample, comprising:
    a light source for emitting a light beam;
    a first optical fiber bundle having a plurality of branched optical fiber bundles for splitting the light beam into a plurality of light beams;
    a plurality of optical fiber probes, each comprising an input end, an input/output end, and an output end, wherein each input end is coupled to each corresponding branched optical fiber bundle of the first optical fiber bundle for receiving each split light beam, and the input/output end is arranged at positions corresponding to a plurality of measuring points of the sample, so as to irradiate each split light beam onto each corresponding measuring point and receive a spectrum reflected from each measuring point; and a high-density channels spectral imaging device comprising a second optical fiber bundle and a multi-channel kernel module for receiving the light beam from the second optical fiber bundle, wherein the second optical fiber bundle has a plurality of branched optical fiber bundles respectively coupling to the corresponding output ends of the optical fiber probes, so as to receive each split light beam reflected from each measuring point, and through the second optical fiber bundle, the light beams incident to the multi-channel kernel module are parallel to an optical axis of the multi-channel kernel module.

19. The high-density channels detecting device as claimed in claim 18, wherein the light source is a broadband white light source.

20. The high-density channels detecting device as claimed in claim 18, wherein the multi-channel kernel module further comprises an optical slit, a collimator lens, a diffraction grating, a focusing lens, and a two-dimensional array sensor arranged on a beam path of the light beam sequentially.

21. The high-density channels detecting device as claimed in claim 20, wherein the collimator lens is an aspherical collimator or a spherical collimator, the diffraction grating is a transmission diffraction grating or a reflection diffraction grating, and the focusing lens is a common focusing lens or an achromatic focusing lens.

22. The high-density channels detecting device as claimed in claim 21, wherein the achromatic focusing lens has a deviation angle about the optical axis of the multi-channel kernel module in an oblique manner the two-dimensional array sensor tilts about the optical axis of the achromatic focusing lens.

23. A high-density channels detecting device for detecting a sample, comprising:

a light source for emitting a light beam;

a first optical fiber bundle having a plurality of branched optical fiber bundles for splitting the light beam into a plurality of light beams;

a plurality of optical fiber probes, each comprising an input end and an output end, wherein each input end is coupled to each branched optical fiber bundle of the first optical fiber bundle for receiving each split light beam, and each of the output ends is arranged at positions corresponding to a plurality of measuring points on the sample, so as to irradiate each split light beam onto each measuring point;

a plurality of second optical fiber probes, each comprising an input end and an output end, wherein each input end is arranged at positions corresponding to the measuring points on the sample, so as to receive a spectrum passing through each measuring point; and a high-density channels spectral imaging device comprising a second optical fiber bundle and a multi-channel kernel module for receiving the light beam from the second optical fiber bundle, wherein the second optical fiber bundle has a plurality of branched optical fiber bundles respectively coupling to the output ends of the second optical fiber probes so as to receive split light beams respectively passed through each of measuring points, and through the second optical fiber bundle, the light beams incident to the multi-channel kernel module are parallel to an optical axis of the multi-channel kernel module.

24. The high-density channels detecting device as claimed in claim 23, wherein the light source is a broadband white light source.

25. The high-density channels detecting device as claimed in claim 23, wherein the multi-channel kernel module further comprises an optical slit, a collimator lens, a diffraction grating, a focusing lens, and a two-dimensional array sensor arranged on a beam path of the light beam sequentially.

26. The high-density channels detecting device as claimed in claim 25, wherein the collimator lens is an aspherical collimator or a spherical collimator, the diffraction grating is a transmission diffraction grating or a reflection diffraction grating, and the focusing lens is a common focusing lens or an achromatic focusing lens.

27. The high-density channels detecting device as claimed in claim 26, wherein the achromatic focusing lens has a deviation angle about the optical axis of the multi-channel kernel module in an oblique manner.

* * * * *